United States Patent
Kim et al.

(10) Patent No.: US 12,357,974 B2
(45) Date of Patent: Jul. 15, 2025

(54) AMMOXIDATION CATALYST FOR PROPYLENE, MANUFACTURING METHOD OF THE SAME CATALYST, AMMOXIDATION METHOD USING THE SAME CATALYST

(71) Applicant: LG CHEM, LTD., Seoul (KR)

(72) Inventors: Ji Yeon Kim, Daejeon (KR); Kyungyeon Kang, Daejeon (KR); Jun Seon Choi, Daejeon (KR)

(73) Assignee: LG CHEM, LTD., Seoul (KR)

( * ) Notice: Subject to any disclaimer, the term of this patent is extended or adjusted under 35 U.S.C. 154(b) by 666 days.

(21) Appl. No.: 17/779,111

(22) PCT Filed: Jul. 29, 2021

(86) PCT No.: PCT/KR2021/009908
§ 371 (c)(1),
(2) Date: May 23, 2022

(87) PCT Pub. No.: WO2022/025675
PCT Pub. Date: Feb. 3, 2022

(65) Prior Publication Data
US 2022/0395817 A1   Dec. 15, 2022

(30) Foreign Application Priority Data

Jul. 29, 2020 (KR) .................. 10-2020-0094652
Jul. 29, 2021 (KR) .................. 10-2021-0099864

(51) Int. Cl.
*B01J 23/887* (2006.01)
*B01J 21/08* (2006.01)
(Continued)

(52) U.S. Cl.
CPC .......... *B01J 23/8873* (2013.01); *B01J 21/08* (2013.01); *B01J 35/23* (2024.01); *B01J 35/613* (2024.01);
(Continued)

(58) Field of Classification Search
CPC ...... B01J 23/8873; B01J 35/23; B01J 35/615; B01J 35/613; B01J 21/08; B01J 37/0221;
(Continued)

(56) References Cited

U.S. PATENT DOCUMENTS 4,297,247 A * 10/1981 Krabetz ............... B01J 23/8885
562/534
4,305,843 A * 12/1981 Krabetz .................. B01J 23/88
502/308
(Continued)

FOREIGN PATENT DOCUMENTS

CN   101690900 A   4/2010
EP   0239071 B1   1/1992
(Continued)

OTHER PUBLICATIONS

English translation of Written Opinion for PCT/KR2021/009908. (Year: 2021).*
(Continued)

*Primary Examiner* — Patricia L. Hailey
(74) *Attorney, Agent, or Firm* — BRYAN CAVE LEIGHTON PAISNER LLP

(57) ABSTRACT

There is provided an ammoxidation catalyst for propylene having a structure in which molybdenum (Mo) oxide is supported first, and an oxide of heterogeneous metals including bismuth (Bi) is supported later. Related methods of making and using the catalyst are also provided.

17 Claims, 1 Drawing Sheet

(51) Int. Cl.
*B01J 35/23* (2024.01)
*B01J 35/61* (2024.01)
*B01J 37/02* (2006.01)
*B01J 37/08* (2006.01)
*C07C 253/26* (2006.01)

(52) U.S. Cl.
CPC ......... *B01J 35/615* (2024.01); *B01J 37/0221* (2013.01); *B01J 37/0228* (2013.01); *B01J 37/0236* (2013.01); *B01J 37/0244* (2013.01); *B01J 37/088* (2013.01); *C07C 253/26* (2013.01)

(58) Field of Classification Search
CPC .............. B01J 37/0228; B01J 37/0236; B01J 37/0244; B01J 37/088; C07C 253/26
USPC ....... 502/206, 240, 243, 246–248, 250, 251, 502/253–260, 305–307, 311–317, 502/319–321
See application file for complete search history.

(56) References Cited

U.S. PATENT DOCUMENTS

| | | | |
|---|---|---|---|
| 6,177,381 B1 | 1/2001 | Jensen et al. | |
| 6,924,387 B1* | 8/2005 | Chang | B01J 23/8876 502/316 |
| 7,943,710 B2* | 5/2011 | Shin | B01J 23/31 526/101 |
| 8,461,074 B2* | 6/2013 | Czaja | B01J 37/0244 502/305 |
| 12,226,753 B2* | 2/2025 | Kang | B01J 35/40 |
| 12,226,757 B2* | 2/2025 | Kim | B01J 35/635 |
| 2003/0236163 A1 | 12/2003 | Chaturvedi et al. | |
| 2004/0082468 A1 | 4/2004 | Suzawa et al. | |
| 2006/0155139 A1 | 7/2006 | Yanagi et al. | |
| 2008/0044329 A1 | 2/2008 | Chen et al. | |
| 2008/0214863 A1* | 9/2008 | Cremer | B01J 23/28 502/312 |
| 2011/0034330 A1* | 2/2011 | Czaja | C07B 35/04 502/311 |
| 2015/0065744 A1 | 3/2015 | Watanabe et al. | |
| 2016/0001228 A1 | 1/2016 | Chang et al. | |
| 2016/0051967 A1 | 2/2016 | Sokolovskii et al. | |
| 2018/0222851 A1 | 8/2018 | Lugmair et al. | |
| 2019/0001309 A1 | 1/2019 | Fukuzawa et al. | |
| 2019/0076829 A1* | 3/2019 | Sprenger | B01J 37/0018 |
| 2019/0168191 A1 | 6/2019 | Aiki et al. | |
| 2021/0316292 A1 | 10/2021 | Moriya et al. | |

FOREIGN PATENT DOCUMENTS

| | | |
|---|---|---|
| JP | 2002502699 | 1/2002 |
| JP | 2004025178 | 1/2004 |
| JP | 2004-154766 A | 6/2004 |
| JP | 2013169482 | 9/2013 |
| JP | 2015157242 | 9/2015 |
| JP | 2017-171659 A | 9/2017 |
| JP | 2019005701 | 1/2019 |
| KR | 19990076301 A | 10/1999 |
| KR | 10-0687671 B1 | 3/2007 |
| KR | 10-2014-0117597 A | 10/2014 |
| KR | 10-1457714 B1 | 11/2014 |
| KR | 10-2016-0002892 A | 1/2016 |
| KR | 10-2017-0026584 A | 3/2017 |
| WO | 2017130906 A1 | 8/2017 |
| WO | 2020039998 A1 | 2/2020 |

OTHER PUBLICATIONS

Teaching Reference Book for Colleges and Universities Applied Physical Chemistry, vol. 3, pp. 236-237, Oct. 31, 1992.

Thanh-Binh et al. "Ammoxidation of Acrolein to Acrylonitrile Over Bismuth Molybdate Catalysts", Applied Catalysis A General, vol. 520 (2016), pp. 7-12.

* cited by examiner

[FIG. 1]
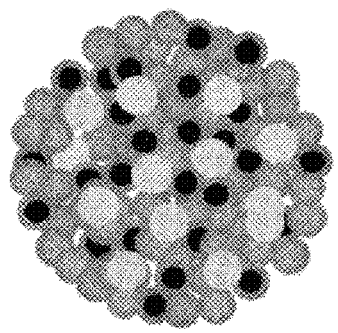
[FIG. 2]
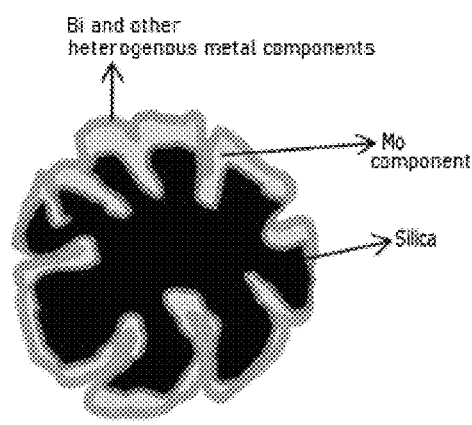

AMMOXIDATION CATALYST FOR PROPYLENE, MANUFACTURING METHOD OF THE SAME CATALYST, AMMOXIDATION METHOD USING THE SAME CATALYST

CROSS-REFERENCE TO RELATED APPLICATION(S)

The present application is a National Phase entry pursuant to 35 U.S.C. § 371 of International Application No. PCT/KR2021/009908 filed on Jul. 29, 2021, and claims priority to and the benefit of Korean Patent Application No. 10-2020-0094652 filed on Jul. 29, 2020, and Korean Patent Application No. 10-2021-0099864 filed on Jul. 29, 2021 with the Korean Intellectual Property Office, the disclosures of which are herein incorporated by reference in their entirety.

FIELD

This invention relates to an ammoxidation catalyst for propylene, a manufacturing method of the same, and an ammoxidation method using the same.

BACKGROUND

Acrylonitrile (AN) is used as one of the raw materials of ABS resin, and can be applied to various chemical products, and thus, worldwide demand and production are increasing.

Such acrylonitrile can be prepared through the ammoxidation reaction of propylene. The ammoxidation reaction of propylene comprises reduction of ammonia and propylene, and reoxidation by oxygen. In order to control heat generated during the reactions, a fluidized bed reactor is generally used.

As an ammoxidation catalyst for propylene, since a Mo (molybdenum)-Bi (bismuth) oxide catalyst has been suggested, catalysts to which metals of various oxidation states are added have been suggested. However, despite diversification of catalyst compositions, due to insufficient studies on the structure and properties, increase in the yield of acrylonitrile was limited.

Specifically, as the preparation method of an ammoxidation catalyst for propylene, a sol-gel process is widely known, wherein a metal precursor solution and silica sol are co-precipitated, and the co-precipitated product is spray dried, and then, calcined.

According to the sol-gel process, a catalyst having a secondary particle structure wherein metal oxide particles and silica particles are agglomerated is prepared, but due to weak binding force of primary particles constituting the secondary particle, it may be easily worn out or split into primary particles and lose catalytic activity. Moreover, parts that can participate in the ammoxidation reaction of propylene are limited to the external surface (namely, surface of secondary particle), and provide small surface area, and thus, a large quantity of ammonia is desorbed from the catalyst surface during the ammoxidation reaction of propylene. Besides, at high temperature (about 400~600° C.) at which the ammoxidation reaction of propylene is progressed, metal oxide components (particularly, Mo) may be easily disassociated and evaporated, and thus, catalytic performance may be easily deteriorated.

Thus, in case a catalyst prepared by a sol-gel process is used, continuous make-up of a catalyst is required during the ammoxidation reaction of propylene, and despite the make-up, there is a limit to increase in the yield of acrylonitrile.

SUMMARY

It is an object of the invention to provide an ammoxidation catalyst for propylene that minimizes metal oxide components (particularly, Mo) dissolution and evaporation from the catalyst during ammoxidation of propylene, and prepare acrylonitrile with higher yield using such a catalyst.

Specifically, according to one embodiment of the invention, there is provided an ammoxidation catalyst for propylene having a structure in which molybdenum (Mo) oxide is supported first, and an oxide of heterogeneous metal including bismuth (Bi) is supported later, a method for manufacturing the same.

The ammoxidation catalyst for propylene according to one embodiment comprises comprising a silica carrier; and metal oxide supported in the silica carrier,
wherein the metal oxide has the whole composition satisfying the following Chemical Formula 1, and
comprises a coating layer comprising molybdenum (Mo) oxide; one or more coating layers comprising heterogeneous metals, positioned on the coating layer comprising molybdenum (Mo) oxide:

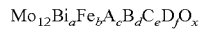  [Chemical Formula 1]

in the Chemical Formula 1,
A is one or more elements of Ni, Mn, and Co,
B is one or more elements of Zn, Mg, Ca, and Ba,
C is one or more elements of Li, Na, K, Rb, and Cs,
D is one or more elements of Cr, W, B, Al, Ca, and V,
a to f, and x are respectively a fraction of atom and atomic group, a is 0.1 to 5, b is 0.1 to 5, c is 0.01 to 10, d is 0.01 to 10, e is 0.01 to 2,
f is 0 to 10, and x is 24 to 48.

The ammoxidation catalyst for propylene may be prepared, for example, by a preparation method comprising the following steps:
supporting molybdenum (Mo) oxide in a silica carrier to prepare a first catalyst; and
supporting oxide of heterogeneous metal in the first catalyst to obtain a catalyst in which metal oxide is supported in a silica carrier.

The catalyst of one embodiment can inhibit dissolution of molybdenum (Mo) and maintain catalytic performance during the ammoxidation reaction of propylene, by the structure in which molybdenum (Mo) oxide is supported first, and an oxide of heterogeneous metal is supported later.

Thus, using the catalyst of one embodiment, acrylonitrile may be produced in large quantities with high yield, without additional supply of catalysts during a propylene ammoxidation process carried out in a fluidized bed reactor.

BRIEF DESCRIPTION OF THE DRAWINGS

FIG. 1 schematically shows a catalyst prepared using a sol-gel process.

FIG. 2 schematically shows a catalyst according to one embodiment.

DETAILED DESCRIPTION

Although various modifications can be made to the invention and the invention may have various forms, specific examples will be illustrated and explained in detail below. However, it should be understood that these are not intended to limit the invention to specific disclosure, and that the invention includes all the modifications, equivalents or replacements thereof without departing from the spirit and technical scope of the invention. In explanation of the invention, in case it is judged that specific explanations regarding related known technologies may obscure the subject matter of the invention, the explanations will be omitted.

And, terms including ordinal numbers such as "a first", "a second" and the like are used to explain various constructional elements, but the constructional elements are not limited by these terms. These terms are used only to distinguish one constructional element from other constructional elements. For example, the first constructional element may be named as the second constructional element, and similarly, the second constructional elements may be also named as the first constructional elements, without departing from the scope of the right of the invention.

A singular expression includes a plural expression thereof, unless it is expressly stated or obvious from the context that such is not intended. As used herein, the terms "comprise" or "have", etc. are intended to designate the existence of practiced characteristic, number, step, constructional element or combinations thereof, and they are not intended to preclude the possibility of existence or addition of one or more other characteristics, numbers, steps, constructional elements or combinations thereof.

Hereinafter, "particle diameter Dv" means a particle diameter at v % point in cumulative volume distribution according to particle diameter. Namely, D50 is a particle diameter at 50% point in cumulative volume distribution according to particle diameter, D90 is a particle diameter at 90% point in the cumulative volume distribution according to particle diameter, and D10 is a particle diameter at 10% point in cumulative volume distribution according to particle diameter.

And, "pore diameter" means the length of a straight line passing the center of pore. And, the silica carrier may comprise multiple pores, and the arithmetic mean of the diameters of multiple pores may be calculated to find average diameter. Alternatively, pore diameter and average pore diameter may be obtained by BJH (Barrett-Joyner-Halenda) method from desorption isotherm of nitrogen gas under liquid nitrogen temperature.

Meanwhile, at the beginning of a catalyst reaction, a process wherein reactants are chemically adsorbed on the catalyst surface is required, and the active sites and surface area of a catalyst are directly connected to adsorption capacity and the resulting chemical reactions. And, although chemisorption on the catalyst surface is slower than physisorption, it tends to increase with increasing temperature.

In this context, ammonia temperature-programmed desorption ($NH_3$-TPD) wherein acid site intensity of a catalyst is measured by the degree of ammonia ($NH_3$) desorption is widely known. In this disclosure, ammonia ($NH_3$) adsorption amount of a catalyst and a carrier may be measured using such ammonia temperature-programmed desorption ($NH_3$-TPD), Hereinafter, an ammoxidation catalyst for propylene of one embodiment will be explained in detail with reference to the drawings.

Ammoxidation Catalyst for Propylene

According to one embodiment of the invention, there is provided an ammoxidation catalyst for propylene having a structure in which molybdenum (Mo) oxide is supported first, and oxide of heterogeneous metal including bismuth (Bi) is supported later.

Specifically, in the catalyst of one embodiment, metal oxide having the whole composition satisfying the following Chemical Formula 1, wherein molybdenum (Mo) is distributed at the lower part (namely, silica carrier side), and heterogeneous metals are distributed on the lower part, is supported in a silica carrier.

    [Chemical Formula 1]

in the Chemical Formula 1,
A is one or more elements of Ni, Mn, and Co,
B is one or more elements of Zn, Mg, Ca, and Ba,
C is one or more elements of Li, Na, K, Rb, and Cs,
D is one or more elements of Cr, W, B, Al, Ca, and V,
a to f, and x are respectively a fraction of atom and atomic group, a is 0.1 to 5, b is 0.1 to 5, c is 0.01 to 10, d is 0.01 to 10, e is 0.01 to 2, f is 0 to 10, and x is 24 to 48.

Commonly known propylene ammoxidation catalysts are prepared by a sol-gel process, and provided as a secondary particle structure in which metal oxide nanoparticles and silica nanoparticles are agglomerated (FIG. 1).

In such a catalyst, metal oxide particles are uniformly distributed inside and outside, but parts capable of participating in propylene ammoxidation reactions are limited to the external surface part (namely, the surface of secondary particle), and a small surface area is provided, and thus, the amount of ammonia desorbed from the catalyst surface during the propylene ammoxidation reaction is large.

On the contrary, if a catalyst is prepared by impregnation, it may be provided as a structure wherein metal oxide is supported in a silica carrier.

The catalyst prepared by impregnation may have smaller fine content than the catalyst prepared by a sol-gel process with the same composition, and excellent durability, without progressing a classification process as a post-treatment after preparation.

However, in case all the metal precursors are simultaneously supported, molybdenum (Mo) may not be sufficiently supported inside the pores of the silica carrier, and $MoO_3$ phase may increase, and thus, it is probable that molybdenum (Mo) may be evaporated or disappear during the ammoxidation reaction of propylene.

Particularly, in the catalyst of one embodiment, in order to lower the probability of evaporation or disappearance of molybdenum (Mo) during the ammoxidation of propylene, molybdenum (Mo) oxide is supported first in the silica carrier, and then, oxide of heterogeneous metals including bismuth (Bi) is sequentially supported (FIG. 2).

Wherein, in order to sequentially support metal oxide, the silica carrier may be mixed a solution of a molybdenum (Mo) metal precursor solution, dried, and calcined, and then, mixed with precursors of heterogeneous metals including bismuth (Bi), dried, and calcined.

For example, if the silica carrier and molybdenum (Mo) precursor solution are mixed, and then, dried to remove the solvent (namely, water), the molybdenum (Mo) precursor may remain on the pore wall of the silica carrier, and the molybdenum (Mo) precursor may be oxidized during the calcination process to form a molybdenum (Mo) oxide layer (coating layer) that continuously coats the pore wall of the silica carrier.

Thereafter, a coating layer of oxide of heterogeneous metals including bismuth (Bi) may be formed by the same method as formation of the molybdenum (Mo) oxide coating layer.

In the catalyst of one embodiment, dissolution of molybdenum (Mo) can be inhibited and catalytic performance can be maintained during the ammoxidation reaction of propylene, by the structure in which molybdenum (Mo) oxide is supported first and an oxide of heterogeneous metals including bismuth (Bi) is supported later.

Thus, using the catalyst of one embodiment, acrylonitrile can be produced in a large quantity with high yield, without additional supply of catalysts during the ammoxidation process of propylene progressed in a fluidized bed reactor.

And, in the catalyst of one embodiment, by controlling the composition of metal oxide so as to further include metals forming active sites of appropriate level for the ammoxidation reaction of propylene, as well as Mo and Bi known to increase the activity of the ammoxidation reaction, catalytic activity can be further increased.

Hereinafter, the catalyst of one embodiment will be explained in more detail.

Structure of Metal Oxide

As explained above, the catalyst of one embodiment may have a structure in which metal oxide wherein molybdenum (Mo) is distributed at the inner part, and bismuth (Bi) and heterogeneous metals are distributed thereon, are supported in a silica carrier, as it is prepared by dividing and supporting metal oxide two times or more.

Specifically, the metal oxide may comprise a coating layer comprising molybdenum (Mo) oxide; and one or more coating layers comprising heterogeneous metals, positioned on the coating layer comprising molybdenum (Mo) oxide.

For example, metal oxide divided and supported two times, may comprise a first coating layer comprising molybdenum (Mo) oxide; and a second coating layer comprising oxide of bismuth (Bi), iron (Fe), element A (A=one or more elements of Ni, Mn, and Co), element B (B=one or more elements of Zn, Mg, Ca, and Ba), and element C (C=one or more elements of Li, Na, K, Rb, and Cs), positioned on the first coating layer.

And, metal oxide divided and supported three times, may comprise a first coating layer comprising molybdenum (Mo) oxide; a second coating layer comprising oxide of bismuth (Bi) and iron (Fe), positioned on the first coating layer; and a third coating layer comprising oxide of element A (A=one or more elements of Ni, Mn, and Co), element B (B=one or more elements of Zn, Mg, Ca, and Ba), and element C (C=one or more elements of Li, Na, K, Rb, and Cs), positioned on the second coating layer.

And, metal oxide divided and supported four times, may comprise a first coating layer comprising molybdenum (Mo) oxide; a second coating layer comprising bismuth (Bi) oxide, positioned on the first coating layer; a third coating layer comprising iron (Fe) oxide, positioned on the second coating layer; and a fourth coating layer comprising oxide of element A (A=one or more elements of Ni, Mn, and Co), element B (B=one or more elements of Zn, Mg, Ca, and Ba), and element C (C=one or more elements of Li, Na, K, Rb, and Cs), positioned on the third coating layer.

However, in any structures, the whole composition of coating layers satisfies the Chemical Formula 1, and metals at the outer and inner parts of adjoining coating layers may be chemically bonded to each other.

For example, although molybdenum (Mo) of the first coating layer may exist in the form of $MoO_3$, it may be bonded to bismuth (Bi) of adjoining second coating layer to form a Mo—Bi—O bond, thereby lowering the probability of evaporation or disappearance of molybdenum (Mo) during the ammoxidation reaction of propylene.

Composition of Metal Oxide

Meanwhile, even if a catalyst has the same structure as the catalyst of one embodiment, if the kind and content of the components constituting the metal oxide do not satisfy the Chemical Formula 1, active sites formed may be insufficient for propylene ammoxidation or excessively dense.

Thus, the kind and content of the components constituting the metal oxide should satisfy the Chemical Formula 1.

Particularly, when the metal oxide is represented by the Chemical Formula 1-1, due to synergistic effects of increasing movement speed of lattice oxygen of molybdenum by Fe to increase conversion, increasing partial oxidation reaction property of propylene due to the formation of complex oxide of Ni and Zn with molybdenum, and dispersing the active sites of complex oxide including K and molybdenum to increase acrylonitrile selectivity, the activity in a propylene ammoxidation reaction may be further increased:

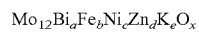

$$Mo_{12}Bi_aFe_bNi_cZn_dK_eO_x \qquad \text{[Chemical Formula 1-1]}$$

In the Chemical Formula 1-1, a to e, and x are respectively fractions of each atom or atomic group, and a is 0.1 to 5, specifically 0.1 to 2.0, b is 0.1 to 5, specifically 0.5 to 3.0, c is 0.01 to 10, specifically 1 to 10, d is 0.01 to 10, specifically 1 to 10, e is 0.01 to 2, specifically 0.01 to 1.0, and x is 24 to 48, specifically 28 to 45.

Weight Ratio of Metal Oxide:Silica Carrier

The catalyst of one embodiment may comprise the metal oxide and the silica carrier at a weight ratio of 15:85 to 35:65, specifically 20:80 to 35:65 (metal oxide:silica carrier).

Within this range, the catalyst of one embodiment may have high activity and high acrylonitrile selectivity.

Silica Carrier

The silica carrier may have pore diameter of 4 nm to 40 nm.

Specifically, when using a silica carrier comprising pores respectively having a diameter of 4 nm or more, 4.2 nm or more, 4.4 nm or more, 4.6 nm or more, 4.8 nm or more, or 5 nm or more, and 40 nm or less, 35 nm or less, 30 nm or less, 25 nm or less, or 20 nm or less, a catalyst exhibiting the above explained pore properties and ammonia adsorption amount can be realized The D50 particle diameter of the silica carrier may be 50 μm to 150 μm. Specifically, the silica carrier may have D50 particle diameter lower limit of 50 μm or more, 51 μm or more, 53 μm or more, or 55 μm or more, and the upper limit of 150 μm or less, 130 μm or less, 110 μm or less, or 90 μm or less.

Structure of a Catalyst

The catalyst of one embodiment may have a structure comprising a silica carrier comprising second pores; an internal coating layer that continuously coats the wall surfaces of the second pores, and comprises metal oxide represented by the Chemical Formula 1; and first pores positioned inside the second pores, and occupying empty spaces except the internal coating layer.

Wherein, the diameter of each second pore may be 4 nm to 40 nm, and the first pores may be determined according to the amount of metal oxide supported in the second pores.

Particularly, the internal coating layer may comprise a coating layer comprising molybdenum (Mo) oxide; and one or more coating layers comprising heterogeneous metals, positioned on the coating layer comprising molybdenum (Mo) oxide, as explained above.

Due to such a support structure, compared to the catalyst prepared by a sol-gel process, the catalyst of one embodiment may have small fine content, excellent durability, low probability of molybdenum (Mo) dissolution, and high activity.

Thus, using the catalyst of one embodiment, acrylonitrile can be obtained with high yield, without additional supply of catalysts during the ammoxidation process of propylene progressed in a fluidized bed reactor.

Specifically, the catalyst of one embodiment may have an egg-shell structure.

For this purpose, a silica carrier comprising a non-porous core part; and a porous shell part positioned on the surface of the non-porous core, and comprising second pores each having a diameter of 2 to 30 nm; may be used.

Specifically, the porous shell comprises depressed parts and protruded parts of the surface, wherein the depressed parts may be formed by opening of the second pores toward the surface of the porous shell.

Thus, the catalyst of one embodiment may have a structure comprising a coating layer that continuously coats the depressed and protruded parts of the porous shell, and comprises metal oxide represented by the Chemical Formula 1; and first pores occupying empty spaces except the coating layer, in the depressed parts of the silica carrier.

The catalyst of one embodiment may have D50 particle diameter lower limit of 30 μm or more, 35 μm or more, 40 μm or more, or 45 μm or more, and the upper limit of 200 μm or less, 190 μm or less, 180 μm or less, 170 μm or less, 160 μm or less, or 150 μm or less.

Ammonia Adsorption Amount of Catalyst

At the beginning of a catalyst reaction, a process wherein reactants are chemically adsorbed on the catalyst surface is required, and the active sites and surface area of a catalyst are directly connected to adsorption capacity and the resulting chemical reactions.

And, although chemisorption on the catalyst surface is slower than physisorption, it tends to increase with increasing temperature.

In this context, ammonia temperature-programmed desorption ($NH_3$-TPD) wherein acid site intensity of a catalyst is measured by the degree of ammonia ($NH_3$) desorption is widely known.

For example, a catalyst is left at 400° C. for about 1 hour to conduct pre-treatment, and then, $NH_3$ is adsorbed to the catalyst at about 100° C. at 10% $NH_3$/He (50 cc/min) for 1 hour, and while flowing He at the same temperature, physiosorbed $NH_3$ is removed, and while raising the temperature to 800° C., desorbed $NH_3$ is measured (b). Wherein, the pre-treatment of the catalyst may be progressed, for example, by filling a catalyst in a device capable of measuring ammonia temperature-programmed desorption, and then, raising the temperature from a room temperature to about 400° C. at the temperature rise speed of 10° C./min using helium gas (50 cc/min), and maintaining at 400° C. for 1 hour.

And then, a difference between the initial adsorption amount (a) and desorption amount (b) of $NH_3$ is calculated to find adsorption amount of $NH_3$ remaining on the catalyst surface.

The catalyst of one embodiment may have ammonia adsorption amount, measured by the above method, of 0.05 mmol/g or more. Such a catalyst having excellent ammonia adsorption capacity may increase propylene conversion and acrylonitrile selectivity during the ammoxidation reaction of propylene, and ultimately, contribute to improvement of acrylonitrile yield.

For example, the catalyst of one embodiment may have ammonia adsorption amount of 0.5 mmol/g or more, 0.53 mmol/g or more, 0.55 mmol/g or more, or 0.57 mmol/g or more, and 5 mmol/g or less, 4 mmol/g or less, 3 mmol/g or less, 2 mmol/g or less, or 1.5 mmol/g or less.

Pore Diameter and BET Specific Surface Area of Catalyst

The catalyst of one embodiment may comprise pores each having a diameter of 4 nm or more, and have BET specific surface area of 100 m²/g or more, while metal oxide of a specific composition is supported in a silica carrier. As the result, compared to the catalyst prepared by a sol-gel process, sites capable of adsorbing ammonia gas and propylene gas may remarkably increase.

As explained above, in the catalyst prepared by a sol-gel process, a site capable of participating in the ammoxidation reaction of propylene is limited to the external surface (namely, the surface of secondary particle), while in the catalyst of one embodiment, a surface area capable of participating in the ammoxidation reaction of propylene is extended to the internal surface (pores) as well as the external surface (namely, catalyst surface).

For example, the catalyst of one embodiment may comprise pores respectively having a diameter of 4 nm or more, 4.1 nm or more, 4.2 nm or more, 4.3 nm or more, 4.4 nm or more, or 4.5 nm or more, and 40 nm or less, 35 nm or less, 30 nm or less, 25 nm or less, 20 nm or less, or 15 nm or less.

And, the catalyst of one embodiment may have BET specific surface area of 100 m²/g or more, 120 m²/g or more, 140 m²/g or more, 160 m²/g or more, 170 m²/g or more, or 175 m²/g or more, and 300 m²/g or less, 270 m²/g or less, 250 m²/g or less, 230 m²/g or less, or 227 m²/g or less.

Method for Manufacturing Ammoxidation Catalyst for Propylene

According to another embodiment of the invention, there is provided a method for manufacturing the above explained catalyst by first supporting molybdenum (Mo) oxide in a silica carrier, and then, supporting heterogeneous metal oxide later.

Specifically, the manufacturing method of one embodiment comprises steps of:

supporting molybdenum (Mo) oxide in a silica carrier to prepare a first catalyst; and supporting oxide of heterogeneous metals in the first catalyst to obtain a catalyst in which metal oxide having the whole composition satisfying the following Chemical Formula 1 is supported in the silica carrier, wherein the metal oxide comprises a coating layer comprising molybdenum (Mo) oxide; and one or more coating layers comprising heterogeneous metal, positioned on the coating layer comprising molybdenum oxide:

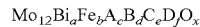    [Chemical Formula 1]

in the Chemical Formula 1,

A is one or more elements of Ni, Mn, and Co,

B is one or more elements of Zn, Mg, Ca, and Ba,

C is one or more elements of Li, Na, K, Rb, and Cs,

D is one or more elements of Cr, W, B, Al, Ca, and V, a to f, and x are respectively a fraction of atom and atomic group, a is 0.1 to 5, b is 0.1 to 5, c is 0.01 to 10, d is 0.01 to 10, e is 0.01 to 2, f is 0 to 10, and x is 24 to 48.

As briefly explained above, in order to sequentially support metal oxide, the silica carrier may be mixed with a molybdenum (Mo) precursor solution, dried and calcined, and then, mixed with the precursors of heterogeneous metals including bismuth (Bi), dried and calcined.

Hereinafter, each step will be explained.

In the manufacturing method of one embodiment, according to the support number of metal oxide, the step of supporting heterogeneous metal oxide in the first catalyst may be conducted as follows.

In case Mo oxide and oxide of other metals are divided and supported (two times), the step of supporting heterogeneous metal oxide in the first catalyst may comprise supporting oxide of bismuth (Bi), iron (Fe), element A (A=one or more elements of Ni, Mn, and Co), element B (B=one or more elements of Zn, Mg, Ca, and Ba), and element C (C=one or more elements of Li, Na, K, Rb, and Cs) in the first catalyst.

In the case of supporting three times, the step of supporting heterogeneous metal oxide in the first catalyst may comprise sequentially supporting oxide of bismuth (Bi) and iron (Fe); and oxide of element A (A=one or more elements of Ni, Mn, and Co), element B (B=one or more elements of Zn, Mg, Ca, and Ba), and element C (C=one or more elements of Li, Na, K, Rb, and Cs) in the first catalyst.

In the case of supporting four times, the step of supporting heterogeneous metal oxide in the first catalyst may comprise sequentially supporting bismuth (Bi) oxide; iron (Fe) oxide; and oxide of element A (A=one or more elements of Ni, Mn, and Co), element B (B=one or more elements of Zn, Mg, Ca, and Ba), and element C (C=one or more elements of Li, Na, K, Rb, and Cs) in the first catalyst.

In each step, supporting of metal oxide may comprise a series of processes of mixing a silica carrier or a catalyst of previous step with a precursor solution, drying and calcining as 1 set, and may consist of 2 or more sets according to the desired support number.

For example, in the case of supporting two times, the silica carrier may be mixed with a molybdenum (Mo) precursor solution, dried and calcined to prepare a first catalyst, and then, the first catalyst may be mixed with a mixed solution of bismuth (Bi), iron (Fe), element A, element B and element C precursors, dried and calcined to obtain the final catalyst.

In the case of supporting three times, the silica carrier may be mixed with a molybdenum (Mo) precursor solution, dried and calcined to prepare a first catalyst; the first catalyst may be mixed with a mixed solution of bismuth (Bi) and iron (Fe) precursors, dried and calcined to prepare a second catalyst; and then, the second catalyst may be mixed with a mixed solution of element A, and element B precursors, dried and calcined to obtain the final catalyst.

In the case of supporting four times, the silica carrier may be mixed with a molybdenum (Mo) precursor solution, dried and calcined to prepare a first catalyst; the first catalyst may be mixed with a bismuth (Bi) precursor solution, dried and calcined to prepare a second catalyst; the second catalyst may be mixed with an iron (Fe) precursor solution, dried and calcined to prepare a third catalyst; and then, the third catalyst may be mixed with a mixed solution of element A, and element B precursors, dried and calcined to obtain the final catalyst.

Hereinafter, processes of manufacture of the metal precursor solution, mixing, drying and calcination will be explained in detail.

Process of Preparing Molybdenum (Mo) Precursor Solution

The step of preparing a molybdenum (Mo) precursor solution may comprise dissolving a Mo precursor in water at 50° C. to 80° C.

The temperature range is sufficient as long as the Mo precursor can be dissolved.

As the molybdenum precursor, for example, a nitrate, an ammonium salt, or an organic complex of molybdenum may be used.

And, in the step of preparing a molybdenum (Mo) precursor solution, one or more water soluble chelating agents selected from citric acid, oxalic acid, tartaric acid, hydrogen peroxide, or a combination thereof, may be added.

The additive functions as an intensity control agent in the catalyst manufacturing process by a sol-gel process, but it functions for transparentizing the molybdenum (Mo) precursor aqueous solution in the above embodiment.

When adding the additive, the weight ratio of the molybdenum precursor and the additive may be 1:0.1 to 1:1, specifically 1:0.2 to 1:0.7, and within this range, solubility of molybdenum precursor may increase, but the ratio is not limited thereto.

Process of Preparing Precursor Solution Other than Molybdenum (Mo) Precursor Solution Precursor solutions other than the molybdenum (Mo) precursor solution may vary according to desired support number.

For example, in order to prepare a mixed solution of bismuth (Bi), iron (Fe), element A, element B and element C precursors used when supporting two times support, a small amount of nitric acid, bismuth (Bi), iron (Fe), element A precursor (A=one or more elements of Ni, Mn, and Co), element B precursor (B=one or more elements of Zn, Mg, Ca, and Ba), and element C precursor (C=one or more elements of Li, Na, K, Rb, and Cs) may be dissolved in water of room temperature.

In case a precursor solution used when supporting three times or four times is prepared, a small amount of nitric acid, and the precursors of the desired metals may be dissolved in water of room temperature.

As the precursors of the elements, a nitrate, an acetate, a chloride, or a hydroxide, etc. of each element may be used.

The processes of preparing the molybdenum (Mo) precursor solution and other precursor solutions are independent, and the preparation sequence is not limited.

However, when preparing each precursor solution, the mixing ratio of precursors may be controlled such that the mole ratio of metals satisfies the Chemical Formula 1, specifically, the stoichiometric mole ratio of the Chemical Formula 1-1.

Mixing Process

When mixing the silica carrier or catalyst of previous step with the precursor solution, they may be mixed at 20° C. to 30° C. for 1 hour to 3 hours, and then, additionally mixed at 70° C. to 90° C. for 1 hour to 3 hours.

By such a support process, the precursor solution may be continuously distributed in the pores of the silica carrier or catalyst of previous step.

Drying Process

The step of drying the mixture of the silica carrier or catalyst of previous step and the precursor solution may be conducted at 90° C. to 130° C. for 10 to 15 hours.

In such a drying process, while the precursor solution is continuously distributed in the pores of the silica carrier or catalyst of previous step, a solvent (namely, water) is removed, and only the precursor may remain.

Calcination Process

The calcination process after the drying process may be conducted at 180° C. to 300° C. for 1 hour to 6 hours when calcining the molybdenum (Mo) precursor, and it may be conducted at 500° C. to 700° C. for 4 to 8 hours when calcining metals other than molybdenum (Mo). If the molybdenum (Mo) precursor calcination temperature exceeds 300° C., all the precursor may be converted into $MoO_3$ phase, and thus, it is preferable that the molybdenum (Mo) precursor calcination temperature is set relatively low, and the temperature of subsequent calcination of heterogeneous metal precursors is increased.

In such a calcination process, while the mixture of precursors is continuously distributed in the pores of the silica carrier or catalyst of previous step, it may be converted into metal oxide of the above explained Chemical Formula 1 (more specifically, Chemical Formula 1-1).

The structure of the catalyst thus formed is as explained above.

Ammoxidation Method for Propylene

According to yet another embodiment of the invention, there is provided a method for ammoxidation of propylene, comprising a step of reacting propylene and ammonia in the presence of the catalyst of the one embodiment as above explained, in a reactor.

The catalyst of one embodiment has high activity and high temperature stability, and may be used for propylene ammoxidation reaction to increase conversion of propylene and selectivity and yield of acrylonitrile.

For the details other than the catalyst of one embodiment, matters commonly known in the art may be referred to, and the detailed explanations thereof are omitted.

Hereinafter, embodiments of the invention will be explained in more detail in the following examples. However, these examples are presented only as the illustrations of the invention, and the scope of the invention is not limited thereby.

EXAMPLES

Example 1 ((Mo)/(Bi, Fe, Ni, Zn, K)/SiO$_2$ Catalyst)

(1) Process of Preparing Mo Precursor Solution 30.3 g of Mo precursor (ammonium molybdate) was dissolved in 99 g of water of 80° C., and 15.13 g of citric acid was added thereto, thus preparing a Mo precursor solution.

(2) Process of Supporting Mo Precursor Solution in Silica Carrier (Impregnation)

Silica (SiO$_2$) particles having particle size of 50 μm, pore diameter of 5.5 nm, pore volume according to nitrogen adsorption of 1.2 cm$^3$/g, and BET specific surface area of 688 m$^2$/g were used as a carrier.

In the (1) Mo precursor solution, 49 g of the silica carrier was introduced, and stirred sequentially at room temperature and 80° C. respectively for 1 hour, so that the Mo precursor solution was sufficiently supported in the pores of the silica carrier.

(3) Process of Preparing Mo/SiO$_2$ Catalyst

Next, the silica carrier in which the Mo precursor solution is supported, prepared in (2), was recovered and dried at a 110° C. oven for 12 hours, and then, heat treated for 6 hours in a tubular calcination furnace of air atmosphere while maintaining a temperature of 200° C., thus obtaining a catalyst in which Mo oxide is supported in a silica carrier (hereinafter, referred to as "Mo/SiO$_2$ catalyst" according to circumstances).

(4) Process of Preparing Mixed Solution of Bi, Fe, Ni, Zn and K Precursors 7.5 g of Fe precursor (iron nitrate) and 13.8 g of Ni precursor (nickel nitrate) were dissolved in 48 g of water of room temperature to prepare a mixed solution of Fe and Ni precursors. In addition, 5.2 g of Bi precursor (bismuth nitrate), 1.3 g of Zn precursor (zinc nitrate), and 0.72 g of K precursor (potassium nitrate) were added to form a mixed solution, and after the solid precursors were dissolved, 2.4 g of nitric acid was further added, and stirred for 30 minutes or more so as to form a transparent solution, thus obtaining a mixed solution of Bi, Fe, Ni, Zn and K precursors.

(5) Process of Supporting Mixed Solution of Bi, Fe, Ni, Zn and K Precursors in Mo/SiO$_2$ Catalyst (Impregnation)

In the Mo/SiO$_2$ catalyst, the (4) mixed solution of Bi, Fe, Ni, Zn and K precursors was introduced, and stirred sequentially at room temperature and 80° C. respectively for 1 hour, so that the mixed solution of Bi, Fe, Ni, Zn and K precursors was sufficiently supported in the pores of the Mo/SiO$_2$ catalyst.

(6) Process of Preparing (Mo)/(Bi, Fe, Ni, Zn, K)/SiO$_2$ Catalyst

Next, the Mo/SiO$_2$ catalyst in which the mixed solution of Bi, Fe, Ni, Zn and K precursors is supported, prepared in (5), was recovered and dried at 110° C. oven for 12 hours, and then, heat treated for 6 hours in a tubular calcination furnace of air atmosphere while maintaining a temperature of 580° C., thus obtaining a catalyst of Example 1 in which Mo oxide, and oxide of Bi, Fe, Ni, Zn and K are sequentially supported in a silica carrier (hereinafter, referred to as "(Mo)/(Bi, Fe, Ni, Zn, K)/SiO$_2$ catalyst" according to circumstances).

(7) Process of Propylene Ammoxidation

In order to activate the catalyst, 0.2 g of the catalyst of Example 1 was filled in a reactor filled with 0.05 g of quartz wool.

While maintaining the internal pressure of the reactor filled with quartz wool and catalyst at atmospheric pressure (1 atm), and increasing the internal temperature of the reactor at the temperature rise speed of 5° C./min, nitrogen and ammonia gas were flowed as a pre-treatment process. The pre-treatment was sufficiently conducted so that the internal temperature of the reactor reached 400° C. at which an ammoxidation reaction can be progressed.

In the pre-treated reactor, while supplying air together with reactants of propylene and ammonia, a propylene ammoxidation process was conducted. Wherein, the amount of reactants supplied was controlled such that the volume ratio of propylene:ammonia:air may become 1:1.0-2.0:1.0-4.0, and total weight hourly space velocity (WHSV) of propylene, ammonia and air may become 1 h$^{-1}$.

After the ammoxidation reaction was completed, the product was recovered, and in order to confirm whether acrylonitrile was properly produced, it was analyzed using various devices.

The analysis method, analysis results will be explained in detail in Experimental Examples described below.

Example 2 ((Mo)/(Bi, Fe, Ni, Zn, K)/SiO$_2$ Catalyst)

(1) Process of Preparing (Mo)/(Bi, Fe, Ni, Zn, K)/SiO$_2$ Catalyst

The catalyst of Example 2 ((Mo)/(Bi, Fe, Ni, Zn, K)/SiO$_2$ catalyst) was prepared by the same method as Example 1, except that the silica carrier was changed.

Specifically, in Example 2, a silica carrier having larger pore diameter and smaller surface area than Example 1 was used. More specifically, silica (SiO$_2$) particles having particle size of 60 μm, pore diameter of 6.0 nm, pore volume according to nitrogen adsorption of 0.98 cm$^3$/g, and BET specific surface area of 645 m$^2$/g were used as a carrier.

(2) Process of Propylene Ammoxidation

A propylene ammoxidation process was conducted using the catalyst of Example 2 instead of the catalyst of Example 1, and then, the product was recovered, and analysis was conducted in the same manner as Example 1.

Example 3 ((Mo)/(Bi, Fe, Ni, Zn, K)/SiO$_2$ Catalyst)

(1) Process of Preparing (Mo)/(Bi, Fe, Ni, Zn, K)/SiO$_2$ Catalyst

The catalyst of Example 3((Mo)/(Bi, Fe, Ni, Zn and K)/SiO$_2$ catalyst) was prepared by the same method as Example 1, except that the heat treatment temperature of step (6) was changed.

Specifically, in Example 3, the heat treatment temperature was increased about 30° C. than Example 1, and heat treatment was conducted at about 610° C.

(2) Process of Propylene Ammoxidation

A propylene ammoxidation process was conducted using the catalyst of Example 3 instead of the catalyst of Example 1, and then, the product was recovered, and analysis was conducted in the same manner as Example 1.

Example 4 ((Mo)/(Bi, Fe)/(Ni, Zn, K)/SiO$_2$ Catalyst)

(1) Process of Preparing (Mo)/(Bi, Fe)/(Ni, Zn, K)/SiO$_2$ Catalyst

The catalyst of Example 4 was prepared by the same method as Example 1, except that the number of support was changed to three times (first—Mo, second—Bi and Fe, third—Ni, Zn and K).

Specifically, 5.2 g of Bi precursor (bismuth nitrate) and 7.5 g of Fe precursor (iron nitrate) were dissolved in 60 g of water of room temperature, and 15 g of nitric acid was added, and then, stirred for 30 minutes or more so as to become a transparent solution, thus preparing a mixed solution of Bi and Fe precursors.

Separately, 13.8 g of Ni precursor (nickel nitrate), 1.3 g of Zn precursor (zinc nitrate), and 0.72 g of K precursor (potassium nitrate) were dissolved in 60 g of water of room temperature, and 15 g of nitric acid was added, and then, stirred for 30 minutes or more so as to become a transparent solution, thus preparing a mixed solution of Ni, Zn and K.

In the Mo/SiO$_2$ catalyst prepared by the same method as Example 1, the mixed solution of Bi and Fe precursors was introduced, and stirred sequentially at room temperature and 80° C. respectively for 1 hour to support the solution of Bi and Fe precursors, and then, dried in a 110° C. oven for 12 hours, and heat treated for 5 hours in a tubular calcination furnace of air atmosphere while maintaining a temperature of 580° C., thus preparing a catalyst in which Mo oxide and Bi and Fe oxide are sequentially supported in a silica carrier (hereinafter, referred to as "(Mo)/(Bi, Fe)/SiO$_2$ catalyst" according to circumstances.

Next, in the (Mo)/(Bi and Fe)/SiO$_2$ catalyst, the mixed solution of Ni, Zn, and K precursors was introduced, and stirred sequentially at room temperature and 80° C. respectively for 1 hour to support the solution of Ni, Zn, and K precursors, and then, dried in a 110° C. oven for 12 hours, and heat treated for 6 hours in a tubular calcination furnace of air atmosphere while maintaining a temperature of 580° C., thus preparing a catalyst in which Mo oxide; Bi and Fe oxide; and Ni, Zn and K oxide are sequentially supported in a silica carrier (hereinafter, referred to as "(Mo)/(Bi, Fe)/(Ni, Zn, K)/SiO$_2$ catalyst" according to circumstances).

(2) Process of Propylene Ammoxidation

A propylene ammoxidation process was conducted using the catalyst of Example 4 instead of the catalyst of Example 1, and then, the product was recovered, and analysis was conducted in the same manner as Example 1.

Example 5 ((Mo)/(Bi)/(Fe, Ni)/(Zn, K)/SiO$_2$ Catalyst)

(1) Process of Preparing (Mo)/(Bi)/(Fe, Ni)/(Zn, K)/SiO$_2$ Catalyst

The catalyst of Example 5 was prepared by the same method as Example 1, except that the number of support was changed to four times (first—Mo, second—Bi, third—Fe and Ni, fourth—Zn and K).

Specifically, 5.2 g of Bi precursor (bismuth nitrate) was dissolved in 60 g of water, and 15 g of nitric acid was added, and then, stirred for 30 minutes or more so as to become a transparent solution, thus preparing a Bi precursor solution.

Separately, 7.5 g of Fe precursor (iron nitrate) and 13.8 g of Ni precursor (nickel nitrate) were dissolved in 60 g of water of room temperature, and 15 g of nitric acid was added, and then, stirred for 30 minutes or more so as to become a transparent solution, thus preparing a mixed solution of Fe and Ni precursors.

And, separately, 1.3 g of Zn precursor (zinc nitrate), and 0.72 g of K precursor (potassium nitrate) were dissolved in 60 g of water of room temperature, and 15 g of nitric acid was added, and then, stirred for 30 minutes or more so as to become a transparent solution, thus preparing a mixed solution of Zn and K precursors.

In the Mo/SiO$_2$ catalyst prepared by the same method as Example 1, the Bi precursor solution was introduced, and stirred sequentially at room temperature and 80° C. respectively for 1 hour to support the Bi precursor solution, and then, dried in a 110° C. oven for 12 hours, and heat treated for 6 hours in a tubular calcination furnace of air atmosphere while maintaining a temperature of 580° C., thus preparing a catalyst in which Mo oxide and Bi oxide are sequentially supported in a silica carrier (hereinafter, referred to as "(Mo)/(Bi)/SiO$_2$ catalyst" according to circumstances).

Next, in the (Mo)/(Bi)/SiO$_2$ catalyst, the mixed solution of Fe and Ni precursors was introduced, and stirred sequentially at room temperature and 80° C. respectively for 1 hour to support the solution Fe and Ni precursors, and then, dried in a 110° C. oven for 12 hours, and heat treated for 6 hours in a tubular calcination furnace of air atmosphere while maintaining a temperature of 580° C., thus preparing a catalyst in which Mo oxide; Bi oxide; and Fe and Ni oxide are sequentially supported (hereinafter, referred to as "(Mo)/(Bi)/(Fe, Ni)/SiO$_2$ catalyst" according to circumstances).

Next, in the (Mo)/(Bi)/(Fe, Ni)/SiO$_2$ catalyst, the mixed solution of Zn and K precursors was supported, dried and heat treated, thus preparing a catalyst of Example 5 in which Mo oxide; Bi oxide; Fe and Ni oxide; and Zn and K oxide are sequentially supported in a silica carrier (hereinafter, referred to as "(Mo)/(Bi)/(Fe, Ni)/(Zn, K)/SiO$_2$ catalyst" according to circumstances).

(2) Process of Propylene Ammoxidation

A propylene ammoxidation process was conducted using the catalyst of Example 5 instead of the catalyst of Example 1, and then, the product was recovered, and analysis was conducted in the same manner as Example 1.

Example 6 ((Mo)/(Bi, Fe, Ni, Zn, K)/SiO$_2$ Catalyst)

(1) Process of Preparing (Mo)/(Bi, Fe, Ni, Zn, K)/SiO$_2$ Catalyst

The catalyst of Example 6 was prepared by the same method as Example 1, except that the amounts of Bi precursor, Fe precursor and Ni precursor used were changed.

Specifically, 8.7 g of Bi precursor (bismuth nitrate), 8.7 g of Fe precursor (iron nitrate), and 13.795 g of Ni precursor (nickel nitrate) were used.

(2) Process of Propylene Ammoxidation

A propylene ammoxidation process was conducted using the catalyst of Example 6 instead of the catalyst of Example 1, and then, the product was recovered, and analysis was conducted in the same manner as Example 1.

Example 7 ((Mo)/(Bi, Fe, Ni, Zn, K)/SiO$_2$ Catalyst)

(1) Process of Preparing (Mo)/(Bi, Fe, Ni, Zn, K)/SiO$_2$ Catalyst

The catalyst of Example 7 was prepared by the same method as Example 1, except that the amounts of Bi precursor, Fe precursor and Ni precursor used were changed.

Specifically, 8.7 g of Bi precursor (bismuth nitrate), 11.5 g of Fe precursor (iron nitrate), and 13.8 g of Ni precursor (nickel nitrate) were used.

(2) Process of Propylene Ammoxidation

A propylene ammoxidation process was conducted using the catalyst of Example 7 instead of the catalyst of Example 1, and then, the product was recovered, and analysis was conducted in the same manner as Example 1.

Comparative Example 1 ((Mo, Bi, Fe, Ni, Zn, K)/SiO$_2$ Catalyst)

(1) Process of Preparing (Mo, Bi, Fe, Ni, Zn, K)/SiO$_2$ Catalyst (Sol-Gel Process)

First, 16 g of Mo precursor (ammonium molybdate) and 1.1 g of oxalic acid were introduced in 10 g of distilled water and heated to about 50° C., thus preparing a Mo precursor solution.

Separately, in 5 g of water of room temperature, 1.73 g of Bi precursor (bismuth nitrate), 2.01 g of Fe precursor (iron nitrate), 0.6533 g of Ni precursor (nickel nitrate), 0.3159 g of Zn precursor (zinc nitrate), and 0.2148 g of K precursor (potassium nitrate) were dissolved to prepare a mixed solution of Bi, Fe, Ni, Zn, and K precursors.

The Mo precursor solution and the mixed solution of Bi, Fe, Ni, Zn, and K precursors were mixed while stirring, and then, 42.4 g of silica sol (LUDOX AS 40, content: 40%, Grace) was added thereto, and the mixture was stirred, and then, spray dried under conditions of 120° C. (inlet) and 230° C. (outlet) using a rotary disk type spray dryer (device name: BUCHI mini spray dryer).

The obtained powder was calcined at 580° C. for 3 hours to finally obtain a catalyst of Comparative Example 1.

(2) Process of Propylene Ammoxidation

A propylene ammoxidation process was conducted by the same method as Example 1, except that the catalyst of Comparative Example 1 was used instead of the catalyst of Example 1.

After the ammoxidation reaction of Comparative Example 1 was completed, the product was recovered, and analysis was conducted in the same manner as Example 1.

Comparative Example 2 ((Mo, Bi, Fe, Ni, Zn, K)/SiO$_2$ Catalyst)

(1) Process for Preparing (Mo, Bi, Fe, Ni, Zn, K)/SiO$_2$ Catalyst (Sol-Gel Process)

The catalyst of Comparative Example 2 was prepared by the same method as Comparative Example 1, except that the amounts of silica sol, Bi precursor, Fe precursor, Zn precursor, and K precursor used were changed.

Specifically, 34 g of silica sol (LUDOX AS 40, solid content: 40%, Grace), 2.1 g of Bi precursor (bismuth nitrate), 3.7 g of Fe precursor (iron nitrate), 0.63 g of Zn precursor (zinc nitrate), and 0.36 g of K precursor (potassium nitrate) were used.

(2) Process of Propylene Ammoxidation

A propylene ammoxidation process was conducted using the catalyst of Comparative Example 2 instead of the catalyst of Comparative Example 1, and then, the product was recovered, and analysis was conducted in the same manner as Comparative Example 1.

Comparative Example 3 ((Mo)/(Bi, Ce, Fe, Mg, Rb)/SiO$_2$ Catalyst)

(1) Process of Preparing (Mo)/(Bi, Ce, Fe, Mg, Rb)/SiO$_2$ Catalyst (Impregnation)

The catalyst of Comparative Example 3 was prepared by the same method as Example 1, except that the amount of Mo precursor used was changed, and a mixed solution of Bi, Ce, Fe, Mg and Rb precursors was used instead of the mixed solution of Bi, Fe, Ni, Zn and K precursors Specifically, when preparing a Mo precursor solution, 18.241 g of Mo precursor (molybdenum nitrate) was used. And, when preparing a mixed solution of Bi, Ce, Fe, Mg and Rb precursors, 3.449 g of Bi precursor (bismuth nitrate), 0.580 g of Ce precursor (cerium nitrate), 13.646 g of Fe precursor (iron nitrate), 14.92 g of Mg precursor (magnesium nitrate), and 0.426 g of Rb precursor (rubidium nitrate) were used.

(2) Process of Propylene Ammoxidation

A propylene ammoxidation process was conducted using the catalyst of Comparative Example 3 instead of the catalyst of Example 1, and then, the product was recovered, and analysis was conducted in the same manner as Example 1.

Comparative Example 4 ((Mo)/(Bi, Fe, Ni, Zn, Mn, La, Pr, K, Cs)/SiO$_2$ Catalyst)

(1) Process of Preparing (Mo)/(Bi, Fe, Ni, Zn, Mn, La, Pr, K, Cs)/SiO$_2$ Catalyst (Impregnation)

The catalyst of Comparative Example 4 was prepared by the same method as Example 1, except that the amount of Mo precursor used was changed, and a mixed solution of Bi, Fe, Ni, Zn, Mn, La, Pr, K, and Cs precursors was used instead of the mixed solution of Bi, Fe, Ni, Zn and K metal precursors.

Specifically, when preparing a Mo precursor solution, 18.241 g of Mo precursor (molybdenum nitrate) was used. And, when preparing a mixed solution of Bi, Fe, Ni, Zn, Mn, La, Pr, K, and Cs precursors, 5.66 g of Bi precursor (bismuth nitrate), 8.8 g of Fe precursor (iron nitrate), 24.01 g of Ni precursor (nickel nitrate), 4.95 g of Zn precursor (zinc nitrate), 2.4 g of Mn precursor (manganese nitrate), 1.44 g of La precursor (lanthanum nitrate), Pr precursor (praseodymium nitrate), 0.674 g of K precursor (potassium nitrate), and 0.325 g of Cs precursor (cesium nitrate) were used.

(2) Process of Propylene Ammoxidation

A propylene ammoxidation process was conducted using the catalyst of Comparative Example 4 instead of the catalyst of Example 1, and then, the product was recovered, and analysis was conducted in the same manner as Example 1.

Comparative Example 5 ((Mo, Bi)/SiO$_2$ Catalyst)

(1) Process of Preparing (Mo, Bi)/SiO$_2$ Catalyst (Impregnation)

The catalyst of Comparative Example 5 was prepared by the same method as Example 1, except that the amount of Mo precursor used was changed, and a Bi precursor solution was used instead of the mixed solution of Bi, Fe, Ni, Zn and K precursors.

Specifically, when preparing a Mo precursor solution, 3 g of Mo precursor (molybdenum nitrate) was used. And, when preparing a Bi precursor solution, 16 g of Bi precursor (bismuth nitrate) was used.

(2) Process of Propylene Ammoxidation

A propylene ammoxidation process was conducted using the catalyst of Comparative Example 5 instead of the catalyst of Example 1, and then, the product was recovered, and analysis was conducted in the same manner as Example 1.

Experimental Example 1: Analysis of Catalyst

Each catalyst of Examples and Comparative Examples was analyzed by the following analysis method, and the analysis results were shown in the following Table 1. For reference, each metal oxide composition and mixing ratio with carrier in the Examples and Comparative Examples were also shown in the following Table 1.

BET specific surface area: Using BET specific surface area measuring device (manufacturing company: BEL Japan, device name: BELSORP_Mini), BET specific surface area of each catalyst of Examples and Comparative Examples was measured.

Specifically, in the device, under liquid nitrogen temperature (77K), adsorption amount until relative pressure (P/P0) of 1 was measured, and desorption amount until relative pressure (P/P0) of 0.03 was measured. The measurement values were applied to BJH equation to calculate the pore volume, diameter and surface area of the catalyst.

Ammonia adsorption amount: Using a device capable of measuring by ammonia temperature-programmed desorption (NH$_3$-TPD) (manufacturing company: Micromeritics, device name: Autochem II 2920), ammonia adsorption amount of each catalyst of Examples and Comparative Examples was measured.

Specifically, a U-shaped quartz tube in the device was filled with about 0.1 g of the catalyst, and the device was connected to a U-shaped reactor, and then, using helium gas (50 cc/min), the temperature was raised from a room temperature to about 400° C. at the temperature rise speed of 10° C./min, and then, maintained at 400° C. for about 1 hour, thus progressing pre-treatment. It is intended to remove organic substances remaining in the catalyst.

After the pre-treatment was finished, NH$_3$ was adsorbed at about 100° C. at 10% NH$_3$/He (50 cc/min) for 1 hour. At the same temperature, while flowing He, physiosorbed NH$_3$ was removed, and while raising the temperature to 800° C., desorbed NH$_3$ was measured.

And then, a difference between the initial adsorption amount (a) and desorption amount (b) of NH$_3$ was calculated to find the adsorption amount of NH$_3$ remaining on the catalyst surface.

TABLE 1

| | | | Catalyst analysis results | | | |
|---|---|---|---|---|---|---|
| | Prep. method | Number of support | Metal oxide composition and mixing ratio with carrier | Pore diameter (nm) | BET specific surface area (m$^2$/g) | Ammonia desorpt. amt. (mmol/g) |
| Example 1 | Impreg. | two times (Mo—Bi, Fe, Ni, Zn, K) | Mo$_{12}$Bi$_{0.75}$Fe$_{1.3}$Ni$_{2.5}$Zn$_{0.3}$K$_{0.5}$O$_y$:25 wt %, SiO$_2$:75 wt % | 8.1 | 217.8 | 0.72 |
| Example 2 | Impreg. | two times (Mo—Bi, Fe, Ni, Zn, K) | Mo$_{12}$Bi$_{0.75}$Fe$_{1.3}$Ni$_{2.5}$Zn$_{0.3}$K$_{0.5}$O$_y$:25 wt %, SiO$_2$:75 wt % | 8.5 | 210.2 | 0.69 |
| Example 3 | Impreg. | two times (Mo—Bi, Fe, Ni, Zn, K) | Mo$_{12}$Bi$_{0.75}$Fe$_{1.3}$Ni$_{2.5}$Zn$_{0.3}$K$_{0.5}$O$_y$:25 wt %, SiO$_2$:75 wt % | 8.6 | 196.5 | 0.63 |
| Example 4 | Impreg. | three times (Mo—Bi, Fe—Ni, Zn, K) | Mo$_{12}$Bi$_{0.75}$Fe$_{1.3}$Ni$_{2.5}$Zn$_{0.3}$K$_{0.5}$O$_y$:25 wt %, SiO$_2$:75 wt % | 7.9 | 225.2 | 0.68 |
| Example 5 | Impreg. | 4 회 (Mo—Bi—Ni, Fe—Zn, K) | Mo$_{12}$Bi$_{0.75}$Fe$_{1.3}$Ni$_{2.5}$Zn$_{0.3}$K$_{0.5}$O$_y$:25 wt %, SiO$_2$:75 wt % | 9.2 | 178.5 | 0.59 |
| Example 6 | Impreg. | two times (Mo—Bi, Fe, Ni, Zn, K) | Mo$_{12}$Bi$_{1.25}$Fe$_{1.5}$Ni$_{3.5}$Zn$_{0.3}$K$_{0.5}$O$_y$:25 wt %, SiO$_2$:75 wt % | 8.4 | 213.1 | 0.66 |
| Example 7 | Impreg. | two times (Mo—Bi, Fe, Ni, Zn, K) | Mo$_{12}$Bi$_{1.25}$Fe$_{2.0}$Ni$_{4.0}$Zn$_{0.3}$K$_{0.5}$O$_y$:25 wt %, SiO$_2$:75 wt % | 8.4 | 212.5 | 0.67 |
| Comp. Example 1 | Sol-gel process | one time (Mo, Bi, Fe, Ni, Zn, K) | Mo$_{12}$Bi$_{0.5}$Fe$_{0.7}$Ni$_{0.5}$Zn$_{0.15}$K$_{0.3}$O$_y$:50 wt %, SiO$_2$:50 wt % | 13.6 | 35.8 | 0.14 |
| Comp. Example 2 | Sol-gel process | one time (Mo, Bi, Fe, Ni, Zn, K) | Mo$_{12}$Bi$_{0.6}$Fe$_{1.3}$Ni$_{0.5}$Zn$_{0.3}$K$_{0.5}$O$_y$:50 wt %, SiO$_2$:50 wt % | 13.8 | 34.6 | 0.14 |
| Comp. Example 3 | Impregnation | two times (Mo—Bi, Ce, Fe, Mg, Rb) | Mo$_{12.4}$Bi$_{0.32}$Ce$_{0.08}$Fe$_{1.52}$Ni$_{6.51}$Mg$_{2.62}$Rb$_{0.13}$:25 wt %, SiO$_2$:75 wt % | 8.2 | 231.8 | 0.40 |

TABLE 1-continued

| | Prep. method | Number of support | Metal oxide composition and mixing ratio with carrier | Pore diameter (nm) | BET specific surface area (m²/g) | Ammonia desorpt. amt. (mmol/g) |
|---|---|---|---|---|---|---|
| Comp. Example 4 | Impregnation | two times (Mo—Bi, Fe, Ni, Zn, Mn, La, Pr, K, Cs) | $Mo_{12}Bi_{0.7}Fe_{1.3}Ni_{5.5}Zn_1Mn_{0.5}La_{0.2}Pr_{0.02}K_{0.4}Cs_{0.1}O_x$:25 wt %, $SiO_2$:75 wt % | 8.4 | 225.3 | 0.41 |
| Comp. e Example 5 | Impregnation | two times(Mo—Bi) | $Bi_2O_3 \cdot MoO_3$:25 wt %, $SiO_2$:75 wt % | 8.1 | 226.4 | 0.22 |

Experimental Example 2: Analysis of Propylene Ammoxidation Product

Using chromatography (Gas chromatography, manufacturing company: Agilent device name: HP 6890 N) equipped with FID (Flame Ionization Detector) and TCD (Thermal conductivity detector), each ammoxidation product of Examples and Comparative Examples was analyzed.

Specifically, with FID, products such as ethylene, hydrogen cyanide, acetaldehyde, acetonitrile, acrolein, acrylonitrile, and the like were analyzed, and with TCD, gas products such as $NH_2$, $O_2$, $CO$, $CO_2$, and the like and unreacted propylene were analyzed, thus calculating the mole number of reacted propylene and the mole number of ammoxidation product in each Example and Comparative Example.

The analysis results and the mole number of propylene supplied were substituted for the following Formulas 1, 2 and 3, thus calculating propylene conversion, and selectivity and yield of acrylonitrile, which is the ammoxidation reaction product of propylene, and the calculation value were shown in the following Table 2.

Propylene conversion (%)=100*(ammoxidation mole number of reacted propylene)/(mole number of supplied propylene)  [Formula 1]

Acrylonitrile selectivity (%)=100*(mole number of produced acrylonitrile)/(mole number of reacted propylene)  [Formula 2]

Acrylonitrile yield (%)=100*(mole number of produced acrylonitrile)/(mole number of supplied propylene)  [Formula 3]

And, Mo reduction rate after the reaction of each Example and Comparative Example was measured as follows, and the measurement results were shown in the following Table 2.

TABLE 2

| | Propylene ammoxidation product | | | |
|---|---|---|---|---|
| | Propylene conversion (%) | Acrylonitrile selectivity (%) | Acrylonitrile yield (%) | Mo reduction rate (%) |
| Example 1 | 87.7 | 75.6 | 66.4 | 0 |
| Example 2 | 85.9 | 76.7 | 65.9 | 0 |
| Example 3 | 87.4 | 75.9 | 66.3 | 0 |
| Example 4 | 87.2 | 74.4 | 64.9 | 0 |
| Example 5 | 76.8 | 77.3 | 59.4 | 0 |
| Example 6 | 80.6 | 78.4 | 63.2 | 0 |
| Example 7 | 79.5 | 78.6 | 62.5 | 0 |
| Comp. Example 1 | 68.3 | 73.3 | 50.5 | 4.2 |
| Comp. Example 2 | 64.2 | 75.8 | 48.6 | 4.0 |
| Comp. Example 3 | 74.3 | 69.5 | 51.6 | 0 |
| Comp. Example 4 | 15.2 | 62.4 | 9.5 | 0 |
| Comp. Example 5 | 12.5 | 58 | 7.3 | 10.3 |

Evaluation

From the Table 2, it is confirmed that the catalysts of Examples 1 to 7, compared to the catalysts of Comparative Examples 1 to 5, have remarkably high propylene conversion and acrylonitrile yield, and do not generate Mo reduction during the ammoxidation reaction of propylene.

Specifically, to sum up the Tables 1 and 2, it can be seen that in the catalysts of Examples 1 to 7 prepared by impregnation, a larger amount of ammonia is adsorbed compared to the catalysts of Comparative Examples 1 to 3 prepared by sol-gel process, thus contributing to increase in propylene conversion and acrylonitrile yield according to the ammoxidation reaction of propylene.

Particularly, it can be seen that since the catalysts of Examples 1 to 7 were prepared by impregnation wherein the support number of metal oxide is controlled to two or more times, they have structures in which molybdenum (Mo) oxide is supported first and heterogeneous metal oxide is supported later, thereby inhibiting dissolution of molybdenum (Mo) during the ammoxidation reaction of propylene.

However, although the catalysts of Comparative Examples 3 to 5 were prepared by the method of controlling the support number of metal oxide to two or more times, they have remarkably low propylene conversion and acrylonitrile yield compared to Examples 1 to 7.

Specifically, in the case of Comparative Example 3 comprising Ce, and the like as active metals; and Comparative Example 4 comprising La, Pr, and the like as active metals, due to the influence of the active metals, propylene conversion and acrylonitrile yield were lowered.

Particularly, in the case of Comparative Example 5 comprising Mo and Bi only as active metals, propylene conversion and acrylonitrile yield were remarkably lowered, and it was difficult to inhibit Mo dissolution by Bi only.

Thus, referring to Examples, by controlling the support number of metal oxide, the whole composition of metal oxide, and the like within the range of the above explained embodiment, catalyst stability may be increased, and propylene conversion, acrylonitrile selectivity and yield may be controlled to desired ranges.

The invention claimed is:
1. An ammoxidation catalyst for propylene comprising:
a silica carrier; and
a metal oxide supported in the silica carrier;
wherein the metal oxide as a whole has a composition satisfying the following Chemical Formula 1, and
comprises a coating layer comprising molybdenum (Mo) oxide, one or more coating layers comprising heterogeneous metals, positioned on the coating layer comprising molybdenum (Mo) oxide·

$$Mo_{12}Bi_aFe_bA_cB_dC_eD_fO_x \qquad \text{[Chemical Formula 1]}$$

in the Chemical Formula 1,
A is one or more elements of Ni, Mn, and Co,
B is one or more elements of Zn, Mg, Ca, and Ba,
C is one or more elements of Li, Na, K, Rb, and Cs,
D is one or more elements of Cr, W, B, Al, Ca, and V,
a to f, and x are respectively a fraction of atom and atomic group, a is 0.1 to 5, b is 0.1 to 5, c is 0.01 to 10, dis 0.01 to 10, e is 0.01 to 2, f is 0 to 10, and x is 24 to 48.

2. The ammoxidation catalyst for propylene according to claim 1,
wherein the metal oxide as a whole has a composition satisfying the Chemical Formula 1, and
comprises a first coating layer comprising molybdenum (Mo) oxide, and a second coating layer comprising oxide of bismuth (Bi), iron (Fe), element A, wherein A is one or more elements of Ni, Mn, and Co), element B, wherein B is one or more elements of Zn, Mg, Ca, and Ba), and element C, wherein C is one or more elements of Li, Na, K, Rb, and Cs, positioned on the first coating layer, or
comprises a first coating layer comprising molybdenum (Mo) oxide, a second coating layer comprising oxide of bismuth (Bi) and iron (Fe), positioned on the first coating layer, and a third coating layer comprising oxide of element A, wherein A is one or more elements of Ni, Mn, and Co, element B, wherein B is one or more elements of Zn, Mg, Ca, and Ba, and element C, wherein C is one or more elements of Li, Na, K, Rb, and Cs, positioned on the second coating layer, or
comprises a first coating layer comprising molybdenum (Mo) oxide; a second coating layer comprising bismuth (Bi) oxide, positioned on the first coating layer; a third coating layer comprising iron (Fe) oxide, positioned on the second coating layer; and a fourth coating layer comprising oxide of element A, wherein A is one or more elements of Ni, Mn, and Co, element B, wherein B is one or more elements of Zn, Mg, Ca, and Ba, and element C, wherein C is one or more elements of Li, Na, K, Rb, and Cs, positioned on the third coating layer.

3. The ammoxidation catalyst for propylene according to claim 1, wherein metals of adjoining coating layers are chemically bonded to each other.

4. The ammoxidation catalyst for propylene according to claim 1, wherein the catalyst comprises:
a silica carrier comprising second pores;
an internal coating layer that continuously coats the wall surfaces of the second pores, and comprises the metal oxide; and
first pores positioned inside the second pores, and occupying empty spaces except the internal coating layer.

5. The ammoxidation catalyst for propylene according to claim 1, wherein the metal oxide as a whole has a composition satisfying the following Chemical Formula 1-1:

$$Mo_{12}Bi_aFe_bNi_cZn_dK_eO_x \qquad \text{[Chemical Formula 1-1]}$$

in the Chemical Formula 1-1, a to e, and x are respectively a fraction of atom and atomic group, a is 0.1 to 5, b is 0.1 to 5, c is 0.01 to 10, dis 0.01 to 10, e is 0.01 to 2, f is 0 to 10, and x is 24 to 48.

6. The ammoxidation catalyst for propylene according to claim 1, wherein a weight ratio of the metal oxide to the silica carrier is 15:85 to 35:65.

7. The ammoxidation catalyst for propylene according to claim 1, wherein the silica carrier comprises pores having a diameter of 4 nm to 40 nm.

8. The ammoxidation catalyst for propylene according to claim 1, wherein the catalyst has a D50 particle diameter of 50 μm to 150 μm.

9. The ammoxidation catalyst for propylene according to claim 1, wherein the catalyst comprises pores having a diameter of 4 nm to 40 nm.

10. The ammoxidation catalyst for propylene according to claim 1, wherein the catalyst has a BET specific surface area of 100 m²/g to 300 m²/g.

11. The ammoxidation catalyst for propylene according to claim 1, wherein the catalyst has ammonia adsorption amount, measured by ammonia temperature-programmed desorption ($NH_3$-TPD), of 0.5 mmol/g to 5 mmol/g.

12. A method for manufacturing an ammoxidation catalyst for propylene comprising steps of:
supporting molybdenum (Mo) oxide in a silica carrier to prepare a first catalyst; and
supporting an oxide of heterogeneous metals in the first catalyst to obtain a catalyst in which metal oxide having a composition as a whole satisfying the following Chemical Formula 1 is supported in the silica carrier,
wherein the metal oxide comprises a coating layer comprising molybdenum (Mo) oxide; and one or more coating layers comprising heterogeneous metals, positioned on the coating layer comprising molybdenum oxide:

$$Mo_{12}Bi_aFe_bA_cB_dC_eD_fO_x \qquad \text{[Chemical Formula 1]}$$

in the Chemical Formula 1,
A is one or more elements of Ni, Mn, and Co,
B is one or more elements of Zn, Mg, Ca, and Ba,
C is one or more elements of Li, Na, K, Rb, and Cs,
D is one or more elements of Cr, W, B, Al, Ca, and V,
a to f, and x are respectively a fraction of atom and atomic group, a is 0.1 to 5, b is 0.1 to 5, c is 0.01 to 10, dis 0.01 to 10, e is 0.01 to 2, f is 0 to 10, and x is 24 to 48.

13. The method for manufacturing an ammoxidation catalyst for propylene according to claim 12,
wherein the step of supporting the oxide of heterogeneous metals in the first catalyst comprises
supporting oxide of bismuth (Bi), iron (Fe), element A, wherein A is one or more elements of Ni, Mn, and Co, element B, wherein B is one or more elements of Zn, Mg, Ca, and Ba, and element C, wherein C is one or more elements of Li, Na, K, Rb, and Cs, in the first catalyst, or
sequentially supporting an oxide of bismuth (Bi) and iron (Fe, an oxide of element A, wherein A is one or more elements of Ni, Mn, and Co, element B, wherein B is one or more elements of Zn, Mg, Ca, and Ba, and element C, wherein C is one or more elements of Li, Na, K, Rb, and Cs, in the first catalyst, or sequentially supporting bismuth (Bi) oxide, iron (Fe) oxide, and oxide of element A, wherein A is one or more elements of Ni, Mn, and Co, element B, wherein B is one or more elements of Zn, Mg, Ca, and Ba, and element C, wherein C is one or more elements of Li, Na, K, Rb, and Cs, in the first catalyst.

14. The method for manufacturing an ammoxidation catalyst for propylene according to claim 12, wherein the step of preparing the first catalyst comprises steps of:

preparing a molybdenum (Mo) precursor solution;

mixing the silica carrier with the molybdenum (Mo) precursor solution;

drying the silica carrier in which the molybdenum (Mo) precursor solution is supported to obtain a silica carrier in which the molybdenum (Mo) precursor is supported; and calcining the silica carrier in which the molybdenum (Mo) precursor is supported.

15. The method for manufacturing an ammoxidation catalyst for propylene according to claim 14, wherein the drying is conducted at 90° C. to 130° C. for 10 to 15 hours, and the calcination is conducted at 180° C. to 300° C. for 1 hour to 6 hours.

16. The method for manufacturing an ammoxidation catalyst for propylene according to claim 12, wherein the step of supporting the oxide of heterogeneous metals in the first catalyst comprises steps of:

preparing a precursor solution of the heterogeneous metals;

mixing the precursor solution of the heterogeneous metals with the first catalyst;

drying the mixture at 90° C. to 130° C. for 10 to 15 hours; and calcining at 500° C. to 700° C. for 4 to 7 hours.

17. A method for ammoxidation of propylene, comprising a step of reacting propylene and ammonia in the presence of the catalyst of claim 1, in a reactor.

* * * * *